United States Patent [19]
Yoshinaga et al.

[11] Patent Number: 5,185,413
[45] Date of Patent: Feb. 9, 1993

[54] PROCESS FOR PRODUCING HIGHLY WATER-ABSORTIVE POLYMERS

[75] Inventors: Kenji Yoshinaga; Toshiko Nakamura; Kiichi Itoh, all of Yokkaichi, Japan

[73] Assignee: Mitsubishi Petrochemical Company Limited, Tokyo, Japan

[21] Appl. No.: 824,870

[22] Filed: Jan. 22, 1992

Related U.S. Application Data

[63] Continuation of Ser. No. 523,561, May 15, 1990, abandoned.

[30] Foreign Application Priority Data

May 16, 1989 [JP] Japan .................................. 1-121685

[51] Int. Cl.$^5$ .............................................. C08F 2/00
[52] U.S. Cl. ...................................... 526/233; 526/240
[58] Field of Search ............................................ 526/233

[56] References Cited

U.S. PATENT DOCUMENTS

| | | | |
|---|---|---|---|
| 2,789,099 | 4/1957 | Rife et al. | 526/233 |
| 4,621,127 | 11/1986 | Denzinger et al. | 526/193 |
| 4,772,671 | 9/1988 | Steeman et al. | 526/233 |
| 4,774,303 | 9/1988 | Denzinger et al. | 526/233 |

FOREIGN PATENT DOCUMENTS

| | | | |
|---|---|---|---|
| 0019097 | 11/1980 | European Pat. Off. | |
| 386393 | 5/1963 | Japan | 526/233 |
| 2034694 | 2/1990 | Japan | 526/233 |

*Primary Examiner*—Joseph L. Schofer
*Assistant Examiner*—N. Sarofim
*Attorney, Agent, or Firm*—Oblon, Spivak, McClelland, Maier & Neustadt

[57] ABSTRACT

There is provided a process for producing a substantially water-insoluble, highly water-absorptive polymer which comprises subjecting an aqueous solution of a monomer comprising as a main component acrylic acid and/or its alkali metal salt to polymerization in the presence of a hypophosphorous acid compound.

10 Claims, No Drawings

PROCESS FOR PRODUCING HIGHLY WATER-ABSORTIVE POLYMERS

This application is a continuation of application Ser. No. 07/523,561, filed on May 15, 1990, now abandoned.

BACKGROUND OF THE INVENTION

1. Field of the Invention

This invention relates to a process for producing highly water-absorptive polymers.

The polymers obtained by the present invention have the highest water absorption capacity ever available not only with respect to pure water but also with respect to various aqueous electrolytic solutions such as physiological salt solution and artificial urine, and are of increased gel strength. Thus, they can advantageously be used for various water-absorptive articles, especially in sanitary fields.

2. Background Art

Highly water-absorptive polymers are synthetic polymers which have recently been used not only for sanitary goods or paper diapers in sanitary fields but also for water retentive materials, dew condensation preventive materials, freshness retentive materials and solvent dehydrating materials in industrial fields as well as in agricultural and horticultural fields, and are now expected to be applied in a wider range of fields.

As such highly water-absorptive polymers, there are known hydrolyzates of starch/acrylonitrile graft copolymers, crosslinked products of carboxymethylcellulose, crosslinked products of polyacrylic acid (or its salts), acrylic acid (or its salts)/vinyl alcohol copolymers, crosslinked products of polyethylene oxide and the like.

In general, the water absorption capacity of a highly water-absorptive polymer can be conceptually expressed by the following equation:

$$\text{Water Absorption Capacity} = \frac{\text{Osmotic Pressure of Ions} + \text{Affinity of High-Molecular Electrolytes for Water}}{\text{Crosslinking Density}}$$

From this equation, it is apparent that the lower the crosslinking density, the higher the water absorption capacity. In the production of highly water-absorptive polymers using acrylic monomers such as acrylic acid and its alkali metal salts as the starting materials, self-crosslinking tends to proceed excessively even without crosslinking agents whereby the resulting polymers often exhibit insufficient water absorption capacity.

The self-crosslinking may be suppressed to some extent by applying moderate polymerization conditions. However, it is then required to exercise sophisticated control over the polymerization conditions, posing another problems in connection with reproducibility, when taking industrially stable production into account.

Thus, in the production of highly water-absorptive polymers with the use of acrylic monomers as the starting materials, self-crosslinking, which is not yet clarified for its mechanism, forms a barrier against water absorption capacity and reproducibility.

SUMMARY OF THE INVENTION

The present invention is intended to provide a process for producing, with improved reproducibility, highly water-absorptive polymers based on polyacrylic acid (or its salts), which is substantially water insoluble and have a remarkably high water absorption capacity and high gel strength.

As a result of intensive studies made to solve the aforesaid problems, it has been found by the present inventors that when acrylic monomers are polymerized in the presence of a hypophosphorous acid compound, self-crosslinking is successfully suppressed, whereby highly water-absorptive polymers showing the highest water absorption capacity ever available not only for pure water but also for various electrolytic solutions and having high gel strength can be obtained with improved reproducibility. The present invention has been accomplished based on such finding.

Thus, the present invention provides a process for producing a water-insoluble and highly water-absorptive polymer which comprises subjecting an aqueous solution of a monomer comprising as a main component acrylic acid and/or its alkali salt to polymerization in the presence of a hypophosphorous acid compound.

DETAILED DESCRIPTION OF THE INVENTION

Monomer

The monomer to be polymerized in the present invention comprises as a main component an acrylic monomer which is subject to self-crosslinking. The term "acrylic monomer" herein refers to acrylic acid and/or its alkali metal salt. The term "alkali metal salt" herein refers to a salt obtained by the neutralization of the carboxyl group of acrylic acid with an alkali metal hydroxide such as sodium hydroxide, potassium hydroxide or lithium hydroxide. In view of the quality, price, etc. of the resulting polymers, particular preference is given to a salt obtained by the neutralization of acrylic acid with sodium hydroxide.

The degree of neutralization of the alkali metal salt is not particularly limited. In order to make the properties of the resulting highly water-absorptive polymers totally well-balanced, however, it is particularly preferred that 50 to 95 mol % of the total carboxyl groups be neutralized.

In accordance with the present invention, if desired, a small amount of other monomers copolymerizable with the acrylic monomer may also be used. Examples of such monomers include methacrylic acid (salt), maleic acid (salt), itaconic acid (salt), acrylamide, 2-acrylamide-2-methylpropane sulfonate, 2-(meth)acryloylethane sulfonate and 2-hydroxyethyl (meth)acrylate. These monomers are used generally in an amount of up to 20 mol % based on the total amount of monomers used.

The acrylic monomer may also be used in combination with a crosslinking agent. As crosslinking agents, use may be made of water-soluble compounds having in the molecule at least two polymerizable unsaturated groups and copolymerizable with the acrylic monomer. Examples include bisacrylamides, e.g., N,N'-methylenebisacrylamide and N,N'-methylenebismethacrylamide and long-chain diacrylates, e.g., ethylene glycol di(meth)acrylate and polyethylene glycol di(meth)acrylate.

These crosslinking agents may be used generally in an amount of about 0.001 to about 0.5% by weight, preferably about 0.005 to about 0.3% by weight based on the amount of an aqueous monomer solution.

In the present invention, the water absorption capacity is substantially determined by the amount of the crosslinking agent used, since self-crosslinking is controlled by the use of a hypophosphorous acid compound. It is thus possible to obtain the end highly water-absorptive polymers with improved reproducibility.

Radical Polymerization Initiator

The preparation of highly water-absorptive polymers according to the present invention is usually carried out with a radical polymerization initiator. Radical polymerization initiators preferably used in the process of the present invention are water-soluble initiators including persulfates, e.g., potassium or ammonium persulfate and azo initiators, e.g., 2,2'-azobis-(2-amidinopropane) dihydrochloride. These water-soluble radical initiators may be used in a mixture thereof, or may be used in the form of a redox type initiator in combination with a reducing agent such as a sulfite or an amine. These radical polymerization initiators are used generally in an amount of about 0.001 to about 5.0% by weight, preferably about 0.01 to about 1.0% by weight based on an aqueous monomer solution.

Hypophosphorous Acid Compound

One primary feature of the process according to the present invention is that the polymerization is carried out in the presence of a hypophosphorous acid compound.

Examples of preferred hypophosphorous acid compounds include hypophosphorous acid, sodium hypophosphite, potassium hypophosphite, calcium hypophosphite, barium hypophosphite, ammonium hypophosphite and the like. However, other metal salts may be used as well. These hypophosphorous compounds may be used singly or as a mixture thereof. These compounds have been found to be chemically involved in the polymerization reaction, acting towards suppression of self-crosslinking of the acrylic monomers, though the mechanism of which has not been fully clarified yet. Since an adequate control of the self-crosslinking of acrylic monomers, which has been done with difficulty in conventional processes, can be made successfully and with ease by the use of the hypophosphorous acid compound, it has become possible by the present invention to produce highly water-absorptive polymers with improved reproducibility.

Moreover, according to the invention, uniform crosslinking in the resulting polymer can be attained, which contributes to enhanced water absorption capacity and gel strength.

Polymerization

In the present invention, polymerization may be carried out in any manner known in the art for producing highly water-absorptive polymers provided that the polymerization is conducted in the presence of the hypophosphorous acid compound. Specifically, for example, polymerization may be performed by the reverse-phase polymerization in which an aqueous monomer solution is suspended in a hydrocarbon solvent and polymerization is carried out in the presence or absence of a surfactant or by the aqueous solution polymerization in which an aqueous monomer solution, as it is, is subjected to polymerization. The concentration of acrylic acid and its alkali metal salt in a monomer solution is preferably 20 to 80%, more preferably 30 to 60%.

No matter what polymerization method may be adopted, the hypophosphorous acid compound is usually added at the stage of preparing the aqueous monomer solution. Although depending upon the concentration and the degree of neutralization of the monomers used, the amount of the hypophosphorous acid compound added is generally about 10 to 10,000 ppm, preferably 100 to 2,000 ppm, as expressed in terms of its concentration in the aqueous monomer solution.

Experimental Examples

The following experimental examples are given to further illustrate the present invention. In the examples the water absorption capacity and gel strength of the highly water-absorptive polymers obtained were measured as follows.

Water Absorption Capacity (1) 0.2 g of a highly water-absorptive polymer was immersed in 1000 g of pure water in a beaker and stirred with a magnetic stirrer for 1-hour water absorption. Thereafter, the beaker content was subjected to normal filtration through a 100-mesh sieve to measure the weight of the filtrate. Water absorption capacity was determined as the weight of pure water absorbed per gram of the highly water-absorptive polymer, by the following equation:

$$\text{Water Absorption Capacity (for pure water) (g/g polymer)} = \frac{\text{Weight of Pure Water (g)} - \text{Weight of Filtrate (g)}}{\text{Weight of Highly Water-Absorptive Polymer (g)}}$$

(2) 1.0 g of a highly water-absorptive polymer was placed in a 400-mesh nylon bag (of 10 cm×10 cm), which was then immersed in 1 liter of 0.9% saline solution for 1 hour. Afterwards, the nylon bag was pulled up and drained off for 15 minutes and then its weight was measured. Based on a weight difference from the weight of a nylon bag containing a blank sample, the water absorption capacity for physiological salt solution was determined as the weight of 0.9% saline solution absorbed in 1 g of the highly water-absorptive polymer. Further, the water absorption capacity for artificial urine was similarly measured using artificial urine in place of 0.9% saline solution.

Gel Strength 100 g of pure water was absorbed in 0.5 g of a highly water-absorptive polymer (i.e. 200-fold absorption). The strength of the polymer gel thus formed was determined using a rheometer (NMR-2002J type made by Fudo Kogyo). The gel strength was determined as the force as measured at the time the cell intruded into the gel.

Polymerization Example (A)

In a four-necked round flask of 500 ml in volume provided with a stirrer, a reflux cooler, a thermometer and a nitrogen gas supply tube, was placed 121 g of cyclohexane, to which was added and dissolved therein 0.9 g of sorbitan monostearate. Afterwards, dissolved oxygen was expelled by blowing a nitrogen gas into the flask.

Separately, 12.3 g of sodium hydroxide with 95% purity dissolved in 79.65 g of water was added to 30 g of acrylic acid in a conical beaker of 300 ml in volume, while externally cooling with ice, thereby neutralizing 70% of the carboxyl groups. In this case, the concentration of the monomer in water corresponded to 30% by weight, as measured on the monomer after neutralization. Then, to this solution were added and dissolved therein a given amount of a crosslinking agent and 0.104 g of potassium persulfate. Thereafter, dissolved oxygen was expelled by blowing a nitrogen gas in the solution.

Next, the content of the conical beaker of 300 ml in volume was added to the content of the above four-necked round flask, followed by mixing under agitation. Then, the internal temperature of the flask was increased in an oil bath while bubbling a nitrogen gas. As a result, the internal temperature reached around 60° C., then rose rapidly and finally reached 75° C. after tens of minutes. While that internal temperature was maintained at 60 to 65° C., reaction was carried out for 3 hours with stirring at 250 rpm. When stirring was stopped, wet polymer particles settled down on the bottom of the round flask. These particles could easily be separated from the cyclohexane phase by decantation.

The separated wet polymer was transferred into a vacuum dryer, where it was heated to 80° to 90° C. to remove cyclohexane and water attached to the polymer. As a result, 40 g of dry polymer powder was obtained.

Polymerization Example (B)

In a four-necked round flask of 500 ml in volume provided with a stirrer, a reflux cooler, a thermometer and a nitrogen gas supply tube, was placed 121 g of cyclohexane, to which was added and dissolved therein 0.9 g of sorbitan monostearate. Afterwards, dissolved oxygen was expelled by blowing a nitrogen gas into the flask.

Separately, 12.3 g of sodium hydroxide with 95% purity dissolved in 48.74 g of water was added to 30 g of acrylic acid in a conical beaker of 300 ml in volume, while externally cooling with ice, thereby neutralizing 70% of the carboxyl groups. In this case, the concentration of the monomer in water corresponded to 40% by weight, as measured on the monomer after neutralization. Then, to this solution were added and dissolved therein a given amount of a crosslinking agent and 0.104 g of potassium persulfate. Thereafter, dissolved oxygen was expelled by blowing a nitrogen gas in the solution.

Next, the content of the conical beaker of 300 ml in volume was added to the content of the above four-necked round flask, followed by mixing under agitation. Then, the internal temperature of the flask was increased in an oil bath while bubbling a nitrogen gas. As a result, the internal temperature reached around 60° C., then rose rapidly and finally reached 75° C. after tens of minutes. While that internal temperature was maintained at 60 to 65° C., reaction was carried out for 3 hours with stirring at 250 rpm. When stirring was stopped, wet polymer particles settled down on the bottom of the round flask. These particles could easily be separated from the cyclohexane phase by decantation.

The separated wet polymer was transferred into a vacuum dryer, where it was heated to 80° to 90° C. to remove cyclohexane and water attached to the polymer. As a result, 40 g of dry polymer powder was obtained.

Polymerization Example (C)

30 g of acrylic acid was placed in a flask of 100 ml in volume, and 58.7 g of a 22.6% aqueous solution of sodium hydroxide was added dropwise thereto under agitation, while externally cooling with ice, to neutralize 80% of acrylic acid. Next, 0.1 g of potassium persulfate was added to the solution and dissolved under agitation at room temperature.

Separately, 163.4 g of cyclohexane and 1.9 g of sorbitan monolaurate were placed in a 500 ml flask provided with a reflux cooler, which had its interior atmosphere replaced beforehand with a nitrogen gas, and they were stirred at room temperature to dissolve the surfactant. Afterwards, the content of the aforesaid 100 ml flask was added dropwise to the content of the 500 ml flask to suspend the former in the latter. After the system was again sufficiently replaced with a nitrogen gas, it was heated for three-hour reaction, while the temperature of an oil bath was maintained at 55° to 60° C. The formed reaction liquid was evaporated to solid under reduced pressure, yielding a fine granular dry polymer.

Polymerization Example (D)

In a four-necked round flask of 500 ml in volume provided with a stirrer, a reflux cooler, a dropping funnel and a nitrogen gas supply tube, was placed 228 ml of n-hexane, to which was added and dissolved therein 1.8 g of sorbitan monostearate. Afterwards, dissolved oxygen was expelled by blowing a nitrogen gas into the flask.

Separately, 13.1 g of sodium hydroxide with 95% purity dissolved in 39 g of water was added to 30 g of acrylic acid in a conical beaker of 300 ml in volume, while externally cooling with ice, thereby neutralizing 75% of the carboxyl groups. In this case, the concentration of the monomer in the aqueous phase corresponded to 45% by weight. Then, to this solution were added and dissolved therein 0.1 g of potassium persulfate. Thereafter, dissolved oxygen was expelled by blowing a nitrogen gas in the solution.

The content of the conical beaker of 300 ml in volume was added to the content of the above four-necked round flask, followed by mixing under agitation. Then, while the internal temperature of the flask was maintained at 60° to 65° C. in an oil bath, reaction was carried out for 6 hours with a successive supply of small proportions of a nitrogen gas. When stirring was stopped after the reaction, wet polymer particles settled down on the bottom of the round flask. Then n-hexane was distilled off under reduced pressure, followed by drying of the remaining wet polymer at a temperature of 80° to 90° C. under reduced pressure to produce 40 g of a dry powdery polymer.

Polymerization Example (E)

100 g of a 43% aqueous solution of monomers comprising 74.95 mol% of sodium acrylate, 25 mol% of acrylic acid and 0.05 mol% of a crosslinking agent was subjected to stationary polymerization with 0.015 g of ammonium persulfate and 0.005 g of sodium bisulfite at 65° C. in a nitrogen atmosphere to obtain a gel-like hydrous polymer. The hydrous polymer was dried at 110° C. under reduced pressure, and was then pulverized with a mixer type pulverizer to obtain a powdery polymer.

Polymerization Example (F)

30 g of acrylic acid was added to 9.24 g of deionized water, and 20.6 g of potassium hydroxide with 85% purity as a neutralizer and a given amount of a crosslinking agent were successively added to the solution to prepare an aqueous solution of potassium acrylate (with a degree of neutralization of 75%) having a concentration of 70% by weight.

While the aqueous solution was held at 70° C., a solution of 0.208 g of 2,2'-azobis (2-amidinopropane) dihydrochloride in 1.0 g of water was added thereto. Immediately thereafter, the resulting product was cast and spread on the surface of the bottom of a cylindrical reactor of about 10 cm in inner diameter (which had been previously maintained at 70° C.). A few seconds later, polymerization was initiated and completed within about 1 minute to obtain a polymer foamed by the heat of polymerization, which was then pulverized into a powdery polymer.

EXAMPLES and COMPARATIVE EXAMPLES

In Polymerization Examples A to F, hypophosphorous acid compounds and optional crosslinking agents were added to the aqueous monomer solutions upon preparation thereof, which were then subjected to polymerization according to the procedures set forth in the Polymerization Examples to produce highly water-absorptive polymers (Examples 1 to 26).

The types and amounts of the hypophosphorous acid compounds and the crosslinking agents used are shown in Table 1.

The highly water-absorptive polymers produced according to Polymerization Examples A to F with addition of crosslinking agents as shown in Table 2 but with no addition of any hypophosphorous acid compound are herein referred to as those of comparative examples (Comp. Examples 1–6).

TABLE 1

| Polymerization Example | Hypophosphorous Acid Compounds Types | Amounts (in ppm relative to aqueous monomer solution) | Crosslinking Agent*) Types | Amounts (in % relative to aqueous monomer solution) |
|---|---|---|---|---|
| Ex. 1 | A | 150 | MBAA | 0.034 |
| Ex. 2 | A | 300 | MBAA | 0.034 |
| Ex. 3 | A Sodium hypophosphite | 300 | MBAA | 0.017 |
| Ex. 4 | A | 300 | MBAA | 0.009 |
| Ex. 5 | A | 300 | A-600 | 0.081 |
| Ex. 6 | A Hypophosphorous Acid | 100 | MBAA | 0.034 |
| Ex. 7 | A Hypophosphorous Acid | 225 | MBAA | 0.034 |
| Ex. 8 | A Calcium Hypophosphite | 300 | MBAA | 0.034 |
| Ex. 9 | B | 200 | MBAA | 0.010 |
| Ex. 10 | B | 400 | MBAA | 0.010 |
| Ex. 11 | B Sodium Hypophosphite | 400 | MBAA | 0.005 |
| Ex. 12 | B | 400 | MBAA | 0.003 |
| Ex. 13 | B | 400 | A-600 | 0.027 |
| Ex. 14 | B Hypophosphorous Acid | 150 | MBAA | 0.010 |
| Ex. 15 | B Calcium Hypophosphite | 400 | MBAA | 0.010 |
| Ex. 16 | B Potassium Hypophosphite | 500 | MBAA | 0.010 |
| Ex. 17 | C | 50 | — | — |
| Ex. 18 | C | 100 | — | — |
| Ex. 19 | C | 150 | MBAA | 0.010 |
| Ex. 20 | C | 150 | A-600 | 0.022 |
| Ex. 21 | D Sodium Hypophosphite | 50 | — | — |
| Ex. 22 | D | 100 | — | — |
| Ex. 23 | E | 300 | TMPTA | 0.167 |
| Ex. 24 | E | 600 | MBAA | 0.073 |
| Ex. 25 | F | 600 | MBAA | 0.014 |
| Ex. 26 | F | 1000 | MBAA | 0.014 |

*) MBAA ... N,N'-methylenebisacrylamide
A-600 ... polyethylene glycol diacrylate (n = 14)
TMPTA ... trimethylopropane triacrylate

TABLE 2

| Polymerization Example | Amounts of Sodium Hypophosphite Added (in ppm relative to aqueous monomer solution) | Crosslinking Agent*) Types | Amounts (in % relative to aqueous monomer solution) |
|---|---|---|---|
| Comp. Ex. 1 | A | — | MBAA | 0.034 |
| Comp. Ex. 2 | B | — | MBAA | 0.010 |
| Comp. Ex. 3 | C | — | — | — |
| Comp. Ex. 4 | D | — | — | — |
| Comp. Ex. 5 | E | — | TMPTA | 0.167 |
| Comp. Ex. 6 | F | — | MBAA | 0.014 |

The results of the water absorption capacity and gel strength of the highly water-absorptive polymers of Examples 1–26 and Comp. Examples 1–6 shown in Tables 1 and 2 are set forth in Tables 3 and 4.

From the results given in Tables 3 and 4, it is apparent that the highly water-absorptive polymers produced by the process of the present invention have increased water absorption capacity and gel strength.

TABLE 3

| | Water Absorption Capacity (g/g-polymer) | | | Gel Strength (g/cm$^2$) |
| --- | --- | --- | --- | --- |
| | Pure Water | Artificial Urine | 0.9% Saline Solution | |
| Ex. 1 | 835 | 51.3 | 73.4 | 16.4 |
| Ex. 2 | 1011 | 62.2 | 89.0 | 14.7 |
| Ex. 3 | 1370 | 85.5 | 122.4 | 12.4 |
| Ex. 4 | 1430 | 49.0 | 77.3 | 7.6 |
| Ex. 5 | 984 | 61.3 | 84.6 | 13.1 |
| Ex. 6 | 852 | 50.8 | 72.9 | 14.3 |
| Ex. 7 | 1009 | 65.4 | 91.2 | 13.9 |
| Ex. 8 | 1025 | 64.9 | 90.2 | 14.8 |
| Ex. 9 | 910 | 46.2 | 66.3 | 15.2 |
| Ex. 10 | 1092 | 55.5 | 80.1 | 13.6 |
| Ex. 11 | 1138 | 64.4 | 93.0 | 10.8 |
| Ex. 12 | 1890 | 44.5 | 88.9 | 9.2 |
| Ex. 13 | 1006 | 52.1 | 75.9 | 12.6 |
| Ex. 14 | 916 | 47.4 | 68.4 | 15.1 |
| Ex. 15 | 1101 | 56.7 | 81.5 | 12.2 |
| Ex. 16 | 1123 | 54.4 | 80.9 | 12.7 |
| Ex. 17 | 861 | 41.2 | 59.4 | 6.9 |
| Ex. 18 | 988 | 55.9 | 79.9 | 5.9 |
| Ex. 19 | 794 | 41.2 | 59.4 | 6.8 |
| Ex. 20 | 776 | 40.6 | 58.0 | 6.1 |
| Ex. 21 | 803 | 40.6 | 57.2 | 7.2 |
| Ex. 22 | 945 | 53.2 | 74.6 | 6.4 |
| Ex. 23 | 606 | 49.2 | 70.3 | 9.1 |
| Ex. 24 | 585 | 48.8 | 69.7 | 8.8 |
| Ex. 25 | 921 | 61.3 | 87.6 | 9.1 |
| Ex. 26 | 1042 | 77.2 | 101.3 | 6.5 |

TABLE 4

| | Water Absorption Capacity (g/g-polymer) | | | Gel Strength (g/cm$^2$) |
| --- | --- | --- | --- | --- |
| | Pure Water | Artificial Urine | 0.9% Saline Solution | |
| Comp. Ex. 1 | 645 | 39.7 | 48.0 | 11.8 |
| Comp. Ex. 2 | 589 | 34.5 | 52.6 | 8.6 |
| Comp. Ex. 3 | 453 | 25.5 | 36.4 | 5.8 |
| Comp. Ex. 4 | 425 | 24.0 | 35.7 | 6.2 |
| Comp. Ex. 5 | 302 | 33.6 | 41.4 | 9.4 |
| Comp. Ex. 6 | 488 | 41.6 | 53.5 | 8.6 |

What is claimed is:

1. In a process for producing a substantially water-insoluble, highly water-absorptive polymer which comprises subjecting an aqueous solution of a monomer comprising as a main component acrylic acid and/or its alkali metal salt to polymerization conditions effective for producing water-insoluble, water-absorptive polymers, the improvement comprising effecting said polymerization in the presence of a hypophosphorous acid compound and from about 0.001 to about 0.5 percent by weight of a crosslinking agent.

2. The process according to claim 1, wherein the monomer comprises as a main component sodium acrylate having a neutralization degree of 50 to 95%.

3. The process according to claim 1, wherein the polymerization is carried out with the use of a radical polymerization initiator.

4. The process according to claim 3, wherein said initiator is a persulfate or an azo compound.

5. The process according to claim 3, wherein said initiator is used in the form of a redox type initiator in combination with a reducing agent.

6. The process according to claim 1, wherein the hypophosphorous acid compound is selected from the group consisting of hypophosphorous acid, sodium hypophosphite, potassium hypophosphite, calcium hypophosphite, barium hypophosphite, and ammonium hypophosphite.

7. The process according to claim 1, wherein the hypophosphorous acid compound is used in an amount of 10 to 10,000 ppm based on the aqueous solution of a monomer.

8. The process according to claim 7, wherein said amount is 100 to 2,000 ppm.

9. The process according to claim 1, wherein the concentration of acrylic acid and/or its alkali metal salt in the aqueous monomer solution is 20 to 80%.

10. The process according to claim 9, wherein said concentration is 30 to 60%.

* * * * *

UNITED STATES PATENT AND TRADEMARK OFFICE
CERTIFICATE OF CORRECTION

PATENT NO. : 5,185,413

DATED : February 9, 1993

INVENTOR(S) : Kenji Yoshinaga et al.

It is certified that error appears in the above-identified patent and that said Letters Patent is hereby corrected as shown below:

On the title page, Item [54] and column 1, lines 2-3,

The title is incorrect, should read as follows: --PROCESS FOR PRODUCING HIGHLY WATER-ABSORPTIVE POLYMERS--

Signed and Sealed this

Second Day of November, 199

Attest:

BRUCE LEHMAN

*Attesting Officer*  Commissioner of Patents and Trademarks